United States Patent [19]
Chardack et al.

[11] Patent Number: 6,131,587
[45] Date of Patent: Oct. 17, 2000

[54] HAND WASHING AND DRYING APPARATUS AND SYSTEM INCLUDING WASTE DISPOSAL APPARATUS AND METHOD

[75] Inventors: William M. Chardack, Gulfstream; Charles A. Pfretzschner, Delray Beach, both of Fla.

[73] Assignee: 144 Limited Partnership, New Canaan, Conn.

[21] Appl. No.: 09/362,215

[22] Filed: Jul. 28, 1999

Related U.S. Application Data

[63] Continuation-in-part of application No. 09/161,371, Sep. 28, 1998, Pat. No. 5,992,430.

[51] Int. Cl.[7] .................................................. B08B 3/04
[52] U.S. Cl. ............... 134/95.2; 134/102.3; 134/115 R; 141/46.01; 141/46.17
[58] Field of Search ............... 134/115 R, 201, 134/113, 102.3, 95.2, 115 G; 241/46.013, 46.17, 46.014, 46.015, 46.016, 46.017, 46.01

[56] References Cited

U.S. PATENT DOCUMENTS

| | | |
|---|---|---|
| Re. 33,810 | 2/1992 | Strieter ...................................... 134/99 |
| 1,732,775 | 10/1929 | Shaver . |
| 2,592,215 | 4/1952 | Wandel ................. 241/46.17 |
| 2,753,121 | 7/1956 | Elfenbein ........................... 241/46.017 |
| 2,826,763 | 3/1958 | Bass .............................................. 4/158 |
| 2,932,459 | 4/1960 | Roe ..................................... 241/46.17 |
| 3,059,815 | 10/1962 | Parsons, Jr. ................................ 222/81 |

(List continued on next page.)

FOREIGN PATENT DOCUMENTS

| | | |
|---|---|---|
| 541398 | 10/1955 | Belgium . |
| 0 087 188 | 8/1983 | European Pat. Off. . |
| 396-039 | 11/1990 | European Pat. Off. . |
| 0 087 188 | 8/1993 | European Pat. Off. . |
| 2388599 | 12/1978 | France ................................ 241/46.17 |
| 5-329065 | 12/1993 | Japan . |
| 1363854 | 8/1974 | United Kingdom ............... 241/46.013 |
| 1409839 | 10/1975 | United Kingdom ................ 141/46.17 |
| 1 584 574 | 2/1981 | United Kingdom . |

OTHER PUBLICATIONS

Invitation To Pay Additional Fees (Restriction Requirement) mailed Dec. 20, 1999.
Notification of Transmittal of Initial Search Report dated Feb. 22, 2000.
PCT Search Report dated May 29, 1997.
WO 92/00428 (WO'428) 241/46.17, Jan. 1992.

*Primary Examiner*—Frankie L. Stinson
*Attorney, Agent, or Firm*—Fitzpatrick, Cella, Harper & Scinto

[57] ABSTRACT

A disposal apparatus for use with a wash station and a towel dispenser includes a liquid source and a waste disposal unit arranged in fluid communication with the liquid source that (i) collects liquid from the liquid source and receives a spent towel dispensed from the towel dispenser, (ii) disintegrates the spent towel and generates a fluid vortex of liquid and disintegrated spent towel, and (iii) exhausts the fluid vortex. A hand washing and drying apparatus comprises a washing and drying chamber including at least one access port providing access for inserting at least one hand to be washed, a wash liquid dispenser in fluid communication with the interior of the washing and drying chamber for dispensing wash liquid within the washing and drying chamber, a blow dryer in fluid communication with the interior of the washing and drying chamber for providing a directed supply of drying air within the washing and drying chamber, a towel dispenser in communication with the interior of the washing and drying chamber for dispensing a towel, e.g., a disposable paper towel, within the chamber, and a waste disposal unit for disintegrating a spent towel dispensed from the towel dispenser and exhausting disintegrated waste through a drain. The apparatus further may include a control device for controlling the operation of the apparatus.

11 Claims, 5 Drawing Sheets

U.S. PATENT DOCUMENTS

| | | | |
|---|---|---|---|
| 3,122,151 | 2/1964 | Chambers | 134/99 |
| 3,220,424 | 11/1965 | Nelson | 134/47 |
| 3,295,769 | 1/1967 | Nilsson | 241/46.17 |
| 3,358,747 | 12/1967 | Lesher et al. | 165/12 |
| 3,363,847 | 1/1968 | Joa | 241/81 |
| 3,699,984 | 10/1972 | Davis | 134/95 |
| 3,744,149 | 7/1973 | Helbling | 34/202 |
| 3,757,806 | 9/1973 | Bhaskar | 134/191 |
| 3,774,853 | 11/1973 | Seifert | 241/46.17 |
| 3,785,523 | 1/1974 | Goldstein | 221/42 |
| 3,918,987 | 11/1975 | Kopfer | 134/95 |
| 3,992,730 | 11/1976 | Davis | 4/187 |
| 4,120,180 | 10/1978 | Jedora | 68/20 |
| 4,219,367 | 8/1980 | Cary, Jr. | 4/628 |
| 4,279,263 | 7/1981 | Pulliam | 134/45 |
| 4,295,233 | 10/1981 | Hinkel et al. | 4/619 |
| 4,398,310 | 8/1983 | Lienhard | 4/623 |
| 4,402,331 | 9/1983 | Taldo et al. | 134/58 R |
| 4,440,185 | 4/1984 | Wiltse | 134/104 |
| 4,453,286 | 6/1984 | Wieland | 15/313 |
| 4,509,543 | 4/1985 | Livingston | 134/113 |
| 4,670,010 | 6/1987 | Dragone | 4/623 |
| 4,688,585 | 8/1987 | Vetter | 134/56 |
| 4,769,863 | 9/1988 | Tegg et al. | 4/619 |
| 4,817,651 | 4/1989 | Crisp et al. | 134/102 |
| 4,847,927 | 7/1989 | Blanc | 4/629 |
| 4,942,631 | 7/1990 | Rosa | 4/623 |
| 5,062,871 | 11/1991 | Lemon, III | 55/259 |
| 5,064,124 | 11/1991 | Chang | 241/33 |
| 5,074,322 | 12/1991 | Jaw | 134/56 |
| 5,193,563 | 3/1993 | Melech | 134/100.1 |
| 5,209,411 | 5/1993 | Dineley et al. | 241/17 |
| 5,213,117 | 5/1993 | Yamamoto | 134/58 R |
| 5,257,423 | 11/1993 | Jacobsen | 4/630 |
| 5,265,628 | 11/1993 | Sage et al. | 4/630 |
| 5,277,208 | 1/1994 | Mansur | 134/56 |
| 5,401,328 | 3/1995 | Schmitz | 134/58 |
| 5,442,867 | 8/1995 | Robinson | 34/90 |
| 5,522,411 | 6/1996 | Johnson | 134/95.2 |
| 5,558,112 | 9/1996 | Strieter | 134/103.2 |
| 5,687,434 | 11/1997 | Tagg | 4/625 |
| 5,702,115 | 12/1997 | Pool | 280/47.35 |
| 5,727,579 | 3/1998 | Chardack | 134/95.2 |
| 5,732,422 | 3/1998 | McAllister et al. | 4/629 |
| 5,772,291 | 6/1998 | Byrd et al. | 312/34.22 |
| 5,860,437 | 1/1999 | Fernie | 134/95.2 |
| 5,863,002 | 1/1999 | Noguchi et al. | 241/46.17 |

HAND WASHING AND DRYING APPARATUS AND SYSTEM INCLUDING WASTE DISPOSAL APPARATUS AND METHOD

The present application is a continuation-in-part of Application Ser. No. 09/161,371 filed Sep. 28, 1998 now U.S. Pat. No. 5,992,430.

BACKGROUND OF THE INVENTION

1. Field of the Invention

The present invention relates generally to hand washing and drying apparatuses and methods, to an automatic hand washing and drying apparatus comprising a self-contained hand washing and drying chamber including in combination a hand washing liquid dispenser, a blow drying apparatus, a towel dispenser and a waste disposal apparatus, and more particularly to a waste disposal apparatus and method for use with various hand washing and drying apparatuses and systems.

The present invention provides an improvement to the automatic hand washing and drying apparatus disclosed and claimed in commonly owned U.S. Pat. No. 5,727,579.

The present invention has particular utility in environments requiring frequent hand washing and drying operations. Examples of such environments include health care facilities, such as medical and dental offices, child care facilities, industrial clean rooms, and the like. The present invention also has particular utility in food handling environments, including food processing and dispensing applications. The present invention also has particular utility in heavily used public rest rooms, for example in airports, bus and train stations, and the like. The hand washing and drying apparatus of the present invention has utility either as a free standing unit or in addition to existing washing facilities, and may be used in any environment that utilizes hand washing and drying. The disposal apparatus and method has utility either with existing wash stations or in combination with a self-containted washing and drying apparatus of the present invention.

2. Related Art

In the mid 19th Century it was first scientifically proved that frequent hand washing could prevent the transmission of a specific disease. Semmelweis, a Hungarian physician working in the maternity clinics of the Vienna General Hospital, observed that the maternal mortality from puerperal fever (sepsis, child bed fever) was very low in the wards of the midwives. Their activities were largely confined to the ward and entailed the frequent washing of hands. In contrast, in the sections staffed by doctors and medical students, the incidence of disease was high and its mortality frightening. Observing that the doctors and students often came into the maternity ward directly from the dissecting rooms, Semmelweis reasoned that they might carry the disease from the dissected cadavers to the patients. He therefore ordered the doctors and students to wash their hands in a chlorine solution before entering the maternity ward. In a few months, the mortality from child bed fever declined dramatically, and the dread disease literally was washed away, decades before the milestone discoveries of microbes, microbial and a sepsis.

Studies also have demonstrated that hand washing is equally as important in many non-medical settings. Current literature in the fields of health care sanitation, and environmental protection contains many studies dealing with the transmission of disease by the hands. For example, studies have shown a significant decrease in disease transmittance in child care centers where children and providers of care are encouraged to wash frequently.

Many hand washing devices, including automatic, combined washing and drying devices are known. For example, U.S. Pat. No. 3,059,815 (Parsons), U.S. Pat. No. 3,992,720 (Davis), U.S. Pat. No. 4,295,233 (Hinkel), and U.S. Pat. No. 5,074,322 (Jaw) relate to hand washing and drying stations having an open configuration for accessing a hand washing device or a hand washing and drying device. U.S. Pat. No. 4,817,651 (Crisp), U.S. Pat. No. 4,402,331 (Taldo), U.S. Pat. No. 3,918,987 (Kopfer), U.S. Pat. No. 3,757,806 (Bhasker) U.S. Pat. No. 4,688,585 (Vetter), U.S. Pat. No. 5,193,563 (Melech), U.S. Pat. No. 4,219,367 (Cary) and U.S. Pat. No. 5,265,628 (Sage) all relate to an automatic, contained, hand washing device generally including a pair of insertion ports for individually receiving a users hands and forearms to wash or wash and dry same.

Although each of the above-discussed devices may have advantages in certain applications, each has drawbacks. Wash stations that are not substantially enclosed often result in splashing of water when used. Drying by means of a towel, now usually made of disposable paper, requires the user to dispose of the towel in a designated receptacle, and often results in undesirable dispersal of wet towels outside of the designated receptacle. Although many hot air blow dryer devices are known, such blow dryer devices generally require a drying cycle in excess of one minute, often too long for the impatient or hurried user. Moreover, air blowing devices not substantially enclosed spray water and disseminate particulate matter into the environment. It is commonly observed that in rest rooms, the wash basin, soap dispenser, towel dispenser and disposal are usually at some distance from each other, resulting in splashing, ineffective use of receptacles, frequent periodic maintenance requirements, and an unclean and unsafe environment, such that the potential user often walks away, even in a setting in which washing of the hands is mandatory.

U.S. Pat. No. 5,442,867 (Robinson), U.S. Pat. No. 3,785,523 (Goldstein) and Japanese Kokai Patent Document No. 5-325065 (Hamabe) each relate to a combination hand drying unit including a blow dryer and a towel or towel dispenser. The Robinson '867 patent discloses the use of a blow dryer provided side-by-side with a paper towel dispenser, the Goldstein '523 patent discloses the use of a blow dryer disposed immediately below a paper towel dispenser, and the Hamabe JP '065 reference discloses the use of a blow dryer provided immediately above a cloth towel. Each of these drying devices provides the advantage of quick drying of the hands using a towel in combination with blow drying means. However, each of these drying devices is provided remote from a washing station, in an open, wall-mounted configuration, which has drawbacks including dispersion of water and particulate matter during the drying operation, and/or accumulation of sold wastes requiring frequent periodic maintenance and waste disposal.

Commonly owned U.S. Pat. No. 5,727,579 (Chardack) remedies many of the above-discussed drawbacks. The Chardack '579 patent discloses an automatic hand washing and drying apparatus including combined blow drying means and towel dispensing means disposed in a washing and drying chamber. The Chardack '579 patent also discloses such a washing and drying apparatus in combination with a vacuum disposal system for collecting spent towels for bulk sanitary disposal.

Although the apparatus disclosed in the Chardack '579 patent provides significant advantages over other conventional automatic washing and drying devices, this apparatus also has a drawback in that it accumulates solid waste and requires periodic maintenance including disposal of the spent towels collected by the vacuum disposal system. Recycling centers generally do not accept used paper towels for recycling. Moreover, the number of regulations governing recycled waste products continues to rise, and disposal of bulk waste paper products presently is expensive.

U.S. Pat. No. 3,363,847 (Joa) discloses a waste disposer that separates disposable paper waste products from non-paper products, disintegrates the paper waste products and disposes of the disintegrated waste either by compacting the waste for salvage or by flushing the disintegrated waste down a sanitary sewer line. The Joa '847 patent disintegrator includes a rotating picker drum having a plurality of pins disposed on the surface of the drum and provided with a slight clearance (e.g., less than 1/32 inch) from a plurality of picker pins provided on an opposing picker wall. Disposable paper waste is fed between the respective opposing picker pins which cooperate to disintegrate the waste paper.

U.S. Pat. No. 1,732,775 (Shaver) discloses a refuse dispenser for use with a sink. The dispenser includes a hopper having a perforated drain cover that opens and closes to allow access for refuse from the sink, a housing having a perforated end plate, and a spiral grinding cylinder for transporting the refuse through the housing from the hopper and through the perforated end plate, thereby grinding the refuse and disposing of the ground refuse into a drain pipe.

Although each of these disposal devices has utility in certain applications, the need exists for an improved, inexpensive and sanitary disposal apparatus and method for use with a hand washing and drying apparatus and system that utilizes disposable paper towels.

SUMMARY OF THE INVENTION

It is therefore an object of the present invention to provide an improved disposal apparatus and method for use with a hand washing and drying apparatus and system.

It is another object of the present invention to provide an improved hand washing and drying apparatus and system.

In one aspect, the present invention provides an improved hand washing and drying apparatus that is self-contained in a closed system.

In another aspect, the present invention provides an improved hand washing and drying apparatus in which splashing of water outside the apparatus is substantially eliminated.

In another aspect, the present invention provides an improved hand washing and drying apparatus in which diffusion of air containing particulate matter to the outside of the apparatus is substantial eliminated.

In another aspect, the present invention provides an improved hand washing and drying apparatus that is inexpensive and easy to make.

In another aspect, the present invention provides an improved hand washing and drying apparatus that is readily adaptable to a wide range of applications.

In another aspect, the present invention provides an improved hand washing and drying apparatus that facilitates compliance with legal and social standards of cleanliness and safety.

In another aspect, the present invention provides an improved hand washing and drying apparatus having reduced maintenance requirements. In another aspect, the present invention provides a waste disposal apparatus and method which disintegrates and liquifies spent towels, and exhausts the liquified disintegrated towels.

In another aspect, the present invention provides a waste disposal apparatus and method which disintegrates and liquifies spent towels in a fluid vortex, and exhausts the liquified disintegrated towels in the fluid vortex.

In one embodiment, an automatic hand washing and drying apparatus of the present invention includes a washing and drying chamber including at least one access port providing access for inserting at least one hand to be washed, a wash liquid dispenser in fluid communication with the interior of the washing and drying chamber that dispenses wash liquid within the washing and drying chamber, a blow drying device in fluid communication with the interior of the washing and drying chamber that provides a directed supply of drying air within the washing and drying chamber, a towel dispenser that communicates with the interior of the washing and drying chamber and dispenses a towel, e.g., a disposable paper towel, within the chamber, and a waste disposal unit that collects spent towels dispensed from the towel dispenser, disintegrates and liquifies the spent towels, and exhausts the liquified disintegrated towels. In a preferred embodiment, the waste disposal unit disintegrates and liquifies the spent towls in a fluid vortex, and exhausts the liquified disintegrated towels in the fluid vortex.

In another aspect, the washing and drying apparatus may include control means for controlling the operation of the apparatus. In one embodiment, the control device may include a sensor, e.g., located at an access port, for detecting the presence of a user's hands and controlling an automatic operation cycle of the wash liquid dispenser, the towel dispenser, the blow drying device and/or the waste disposal. In another embodiment, the control means may include external control devices, such as foot pedals, for individually controlling the operation of the wash liquid dispenser, the towel dispenser, the blow drying device, and the waste disposal.

In another embodiment, a disposal apparatus of the present invention is provided for use with an existing wash station. The disposal apparatus may be arranged either with independent plumbing or in fluid communication with the wash station.

These and other objects, aspects, advantages and features of the present invention readily will be understood and appreciated when viewed in conjunction with the following detailed description of the preferred embodiments and the accompanying drawings.

DETAILED DESCRIPTION OF THE PREFERRED EMBODIMENTS

Figure 1:
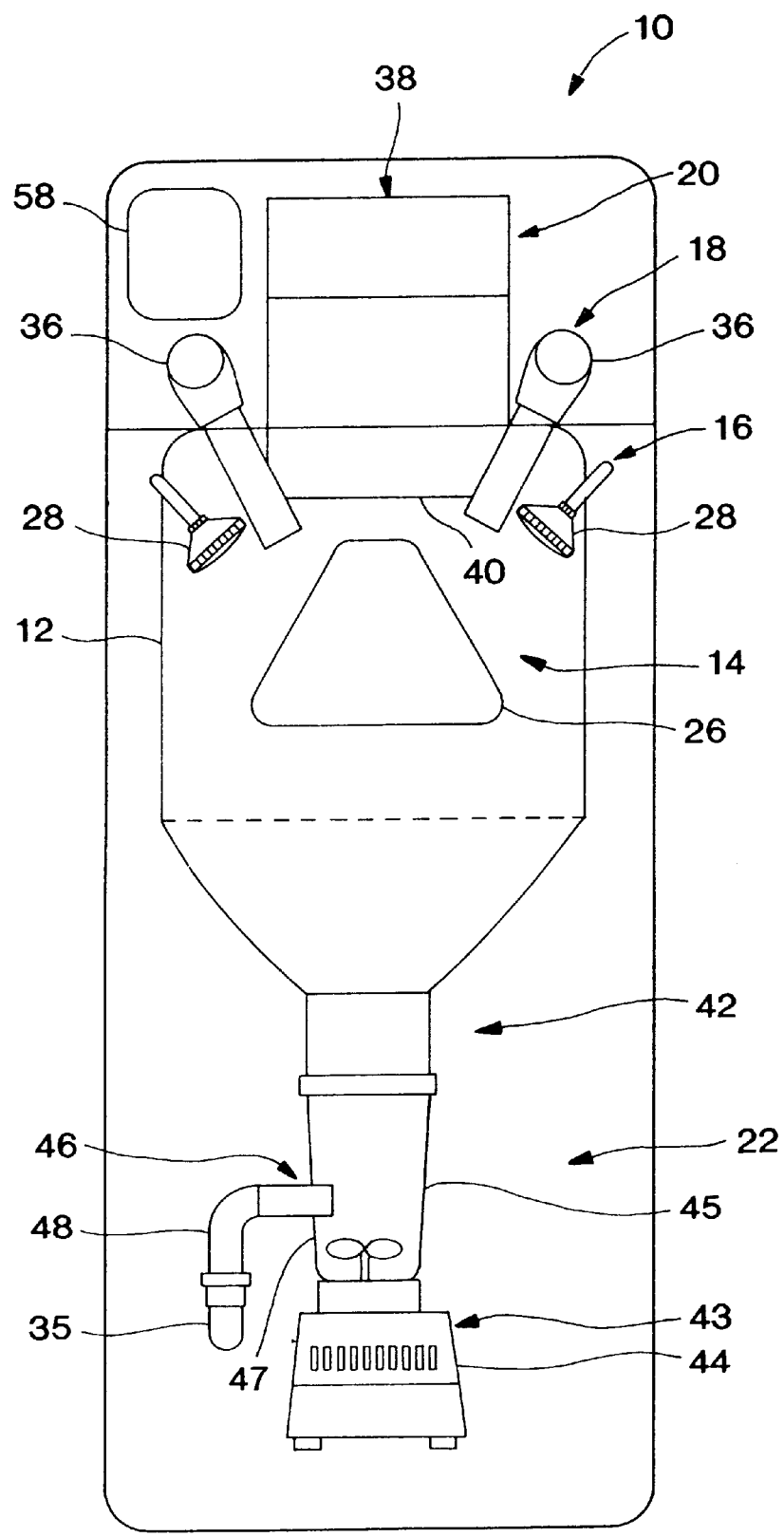
FIG. 1 is a front view schematically illustrating a first embodiment of a hand washing and drying apparatus of the present invention, utilizing a diposal apparatus and method of the present invention.
Figure 2:
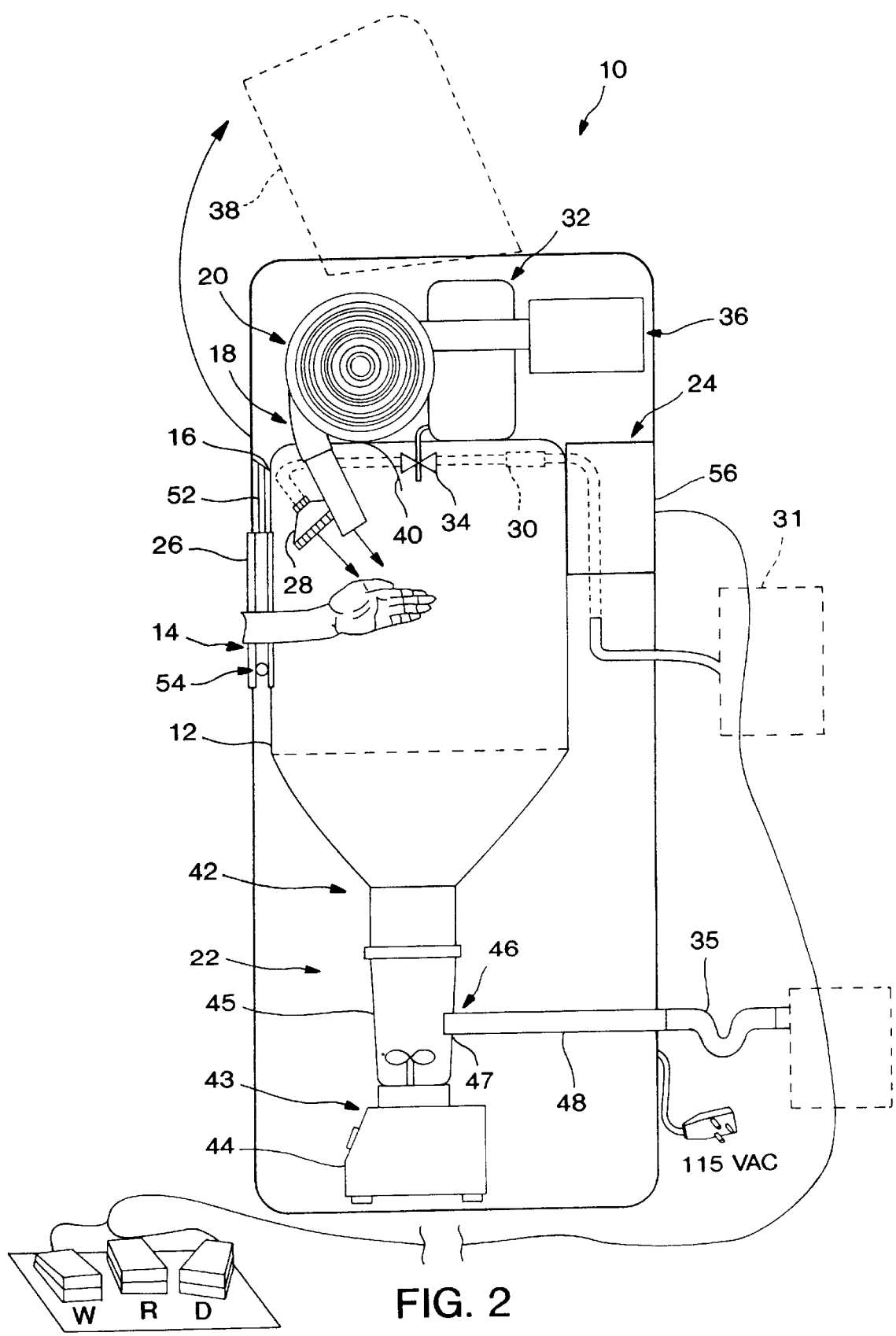
FIG. 2 is a side view schematically illustrating in cross-section the hand washing and drying apparatus and disposal apparatus and method of FIG. 1.

Referring now to the drawings, wherein like or similar reference numerals designate like or similar elements throughout the application, FIGS. 1 and 2 illustrate a preferred embodiment of the present invention.

FIG. 1 is a front view schematically illustrating an embodiment of a hand washing and drying apparatus of the present invention, and FIG. 2 is a side view schematically illustrating in cross-section the hand washing and drying apparatus of FIG. 1. As shown therein, the hand washing and drying apparatus 10 generally includes a washing and drying chamber 12 including chamber access means 14, wash liquid dispensing means 16, blow drying means 18, towel dispensing means 20, and waste disposal means 22. The washing and drying apparatus preferably also includes control means 24 for controlling the washing and drying apparatus 10.

In the embodiment of FIGS. 1 and 2, the washing and drying chamber 12 is a contained (substantially closed) chamber, and includes an access port 26 for insertion of the user's hands. In one embodiment, the access port is generally rectangular (preferably truncated at the top apex, as shown in FIG. 1) to permit both physical and visual access to the interior of the washing and drying chamber 12. Alternatively, the chamber 12 could be provided with plural access ports for individual entry of the hands. The washing and drying apparatus, including the washing and drying chamber 12, may be made of any material suitable for the intended environment, such as plastic, metal, and the like. In the preferred embodiment, the apparatus and housing is made of a molded plastic for ease of manufacture and reduced cost. Those skilled in the art readily will be able to select the various alternative materials and method of manufacture, as well as structure of the access port, to achieve any desired configuration.

The wash liquid dispensing means 16 of FIGS. 1 and 2 includes a pair of shower heads 28, a supply line 30, a water source 31 and a soap dispenser 32. In the present embodiment two shower heads 28 are provided on opposite sides of the washing and drying chamber 12 above and proximate the access port 26, so that washing liquid is dispensed in a direction into the interior of the chamber 12 (toward the users hands) and generally away from the access port 26, to maximize efficient washing of the user's hands and minimize or eliminate spraying of washing liquid out of the chamber 12. The soap dispenser 32 preferably is a liquid soap dispenser and may be provided separately and/or in fluid communication with the water supply line 30, e.g., by a valve 34, so that liquid soap in the soap dispenser 32 may be drawn out of the soap dispenser 32 with the supply of water through the water supply line 30 in a controlled manner. Each of these elements is conventionally available, and those skilled in the art readily will be able to select alternative shower heads 28, soap dispensers 32 and valves 34 (or other means for selectively dispensing washing liquid and soap into the interior of the washing and drying chamber 12), as well as their location and orientation, for achieving the desired application of soap and washing liquid. The water source 31 may be an existing plumbing line or a self-contained water source provided as a portion of the apparatus 10 (shown in phantom in FIG. 2). Likewise, a drain 35 and drain line may be provided to existing plumbing lines, e.g., a standard 1½ inch diameter sink line or a 4 inch diameter sewage line. Alternatively, the drain line may empty into a holding tank for storage of used wash liquid (shown in phantom in FIG. 2). The storage tank may be a conventional septic holding tank or a portion of the apparatus 10. In this manner, it will be apparent that the apparatus 10 may be configured as a fixed unit, a mobile unit attachable to an existing plumbing fixture (sink/drain), or a self-contained mobile unit. Those skilled in the art readily will be able to adapt the apparatus of the present invention to numerous desired environments.

The blow drying means 18 of the present embodiment generally includes a pair of hot air blow dryers 36. Like the shower heads 28, the hot air blow dryers 36 preferably are located on opposite sides of the washing and drying chamber 12 and oriented to direct a stream of heated air in a direction into the interior of the chamber 12 (toward the user's hands) and generally away from the access port 26. While in the preferred embodiment the blow dryers 36 blow hot or heated air, in some applications it may be sufficient merely to provide a stream of air at room temperature. Those skilled in the art readily will be able to adapt conventional blow dryers to achieve any desired configuration and application of drying air to the user's hands.

Figure 3:
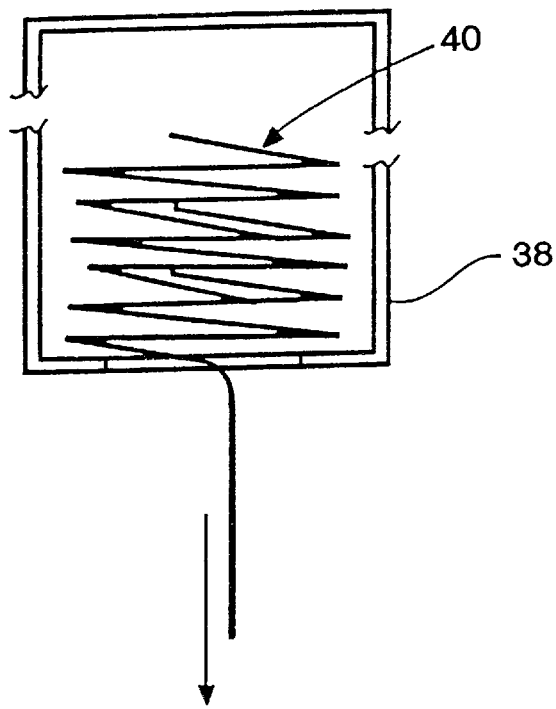
FIG. 3 is an enlarged schematic view of a towel dispensing device of the hand washing and drying apparatus of FIGS. 1 and 2, utilizing a plurality of individual towels interleaved.
Figure 4:
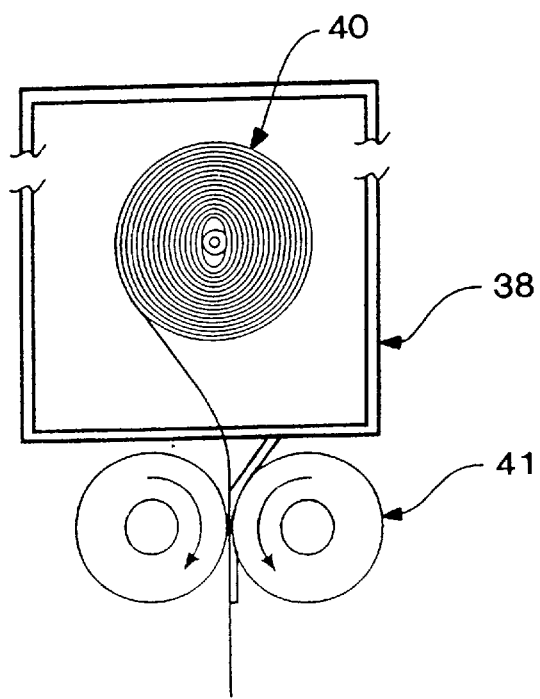
FIG. 4 is an enlarged schematic view of an alternative towel dispensing device of the hand washing and drying apparatus of FIGS. 1 and 2, utilizing a continuous roll of towels fed one-by-one by a motor driven roller.

FIGS. 3 and 4 illustrate two alternative embodiments of towel dispensing means 20 which may be utilized in the embodiment of FIGS. 1 and 2. In each embodiment, the towel dispensing means 20 includes a towel dispenser housing or container 38 and a plurality of towels 40.

The towel dispenser container 38 preferably is disposed in an upper portion of the washing and drying apparatus 10 above the washing and drying chamber 12 and proximate the access port 26. This allows the user to reach up to obtain a towel 40 without withdrawing the hands from the washing and drying chamber 12. This location also minimizes any splashing of water from the wash liquid dispensing means 14 on the towels 40.

In the embodiment of FIG. 3, the towel dispensing means 20 includes a towel dispenser housing 38 that contains a plurality of individual towels 40 folded in an interleaved manner. The plurality of towels 40 thus may be manually dispensed one-by-one into the interior of the chamber 12, and the user is free to use as many towels as desired.

In the embodiment of FIG. 4, the towel dispensing means 20 includes a towel dispenser housing 38 that contains a continuous roll of towels 40, e.g., prescored or perforated to permit dispensing one-by-one. The towel dispensing means 20 also is shown including an optional pair of motor driven rollers 41, to facilitate dispensing of the towels 40 one-by-one.

In the preferred embodiment, the towels 40 are disposable paper towels. The present inventors have identified Georgia-Pacific ® C-Fold Bleach Paper Towels (designated for aircraft use) as particularly suitable for the present embodiment because such towels are soft, absorbent, and readily disintegrate/dissolve in a liquid environment (see discussion of towel waste processing below). However, those skilled in the art readily will be able to identify alternative towels having a softness, absorbency and propensity to disintegrate/dissolve sufficient to satisfy the objectives of the present invention in various environments.

In the embodiment of FIGS. 1 and 2, the waste disposal means 22 generally includes a collection port 42 and an exhaust port 46, and is provided in-line between the washing and drying chamber 12 and the drain 35. The waste disposal means 22 is provided in fluid communication with the interior of the washing and drying chamber 12 via the collection port 42, to collect and evacuate waste therefrom. The waste may include spent washing liquid (e.g., water and soap) and spent towels dispensed from the towel dispensing means 20. Thus, it will be appreciated that the washing and drying chamber provides a liquid source for the waste disposal means, as well as an extended collection port for collecting spent towels.

The waste disposal means 20 is operated in a manner and for a time sufficient to collect any waste matter to be evacuated from the washing and drying chamber 12, including wash water and spent towels 40, to disintegrate any waste matter, including spent paper towels, to substantially liquify such waste matter, and to discharge such waste matter through the discharge port 46 and the drain 35.

In the embodiment illustrated in FIGS. 1 and 2, the disposal means 22 includes a blender 43, such as a conventional Osterizer® Imperial Cycle kitchen blender, including a base (with a motor and rotor/blade) 44 and a blender cup 45. The open end (top) of the blender cup 45 is provided in fluid communication with the interior of the washing and drying chamber 12, thereby forming a collection port 42 through which any waste matter in the washing and drying chamber may be collected. An opening 47 is formed in the side wall of the blender cup 45 and a waste fluid exhaust line 48 is provided in fluid communication with the interior of the blender cup through this opening 47, thereby forming an exhaust port 46 through which waste water and disintegrated waste matter may be exhausted/discharged from the blender cup 45 to the drain 35. When operated, used wash water and any waste matter from the interior of the washing and drying chamber 12 is collected in the blender cup 45 and liquified by disintegrating the waste matter and blending it with the used wash water in the blender cup 45 sufficient to allow the waste water and disintegrated waste matter to flow without clogging through the waste fluid exhaust line 48. It will be appreciated that this blending operation causes the waste water and disintegrated waste matter to form a fluid vortex in the blender cup 45. In this manner, the blender 43 acts as a centrifugal pump to exhaust/discharge the waste water and disintegrated waste matter out through the exhaust port 46 and exhaust line 48 to the drain 35.

Those skilled in the art readily will appreciate that the amount or degree of processing (disintegration/blending/ liquification) required will depend on the characteristics of the paper towel, the disposal unit of the disposal means, and the drain. Paper towels having a greater propensity to disintegrate/dissolve require less processing. Likewise, a standard 4 inch diameter sewage line requires less processing than a standard 1½ inch diameter sink plumbing line.

Numerous waste disposal units/devices are known and commercially available. Alternative waste disposal devices, including a conventional kitchen sink garbage disposal (Grind All® Model GA-1-0) and a marine macerator (West Marine® Model No. 185449), have been successfully used as alternative embodiments of the disposal means of the present invention under various conditions. Other laboratory, industrial, and commercial disintegrators may be desirable in certain environments. Those skilled in the art will be able to select a waste disposal unit appropriate for the desired environment or application. However, the preferred embodiment disclosed herein provides particular and significant advantages over other embodiments because it uses readily available parts that are inexpensive and easy to assemble.

The washing and drying chamber 12 optionally may be provided with a clear window panel to allow the user to observe his or her hands within the chamber 12. The interior face of the panel 52 may be treated or coated so that it is hydrophilic, to facilitate sheeting action of washing liquid that splashes onto the panel, thereby permitting clear viewing and eliminating a claustrophobic effect often experienced with conventional, automatic, self-contained washing and drying system.

In operation, a user's hands are inserted into the hand washing and drying chamber 12 through the access port 26, which insertion is detected by sensors 54 located at the access port 26. The sensors 54 provide a detection signal to a control unit 56 of the control means 24, such as a microprocessor, which initiates a washing cycle. In the washing cycle, water is provided from the water supply line 30 to the pair of shower heads 28 to spray the user's hands resident in the washing and drying chamber 12, and soap is either directly applied to the hands or applied via valve 34 and water supply line 30. In one embodiment, the control unit 56 controls the valve 34 to provide an appropriate supply of soap during at least a portion of the washing cycle.

Upon completion of the washing cycle, the control unit initiates a drying cycle. In the drying cycle, the user first reaches up and withdraws a single towel from the towel dispenser housing 38 (FIG. 3 embodiment). Alternatively, the motor driven rollers 41 of the towel dispensing means 20 are activated by a control signal from the control unit 56, and the motor driven rollers 38 are rotated to advance a single towel 40 from the towel dispenser housing 38 so that it is accessible to the user's hands (FIG. 4 embodiment). The user then rubs and/or lightly dabs his or her hands with the towel 40 to remove a substantial portion of the washing liquid from the hands. The control unit 56 meanwhile continues the drying cycle by activating the pair of blow dryers 36 to provide one or more directed streams of drying air onto the user's hands. Of course, this portion of the drying cycle may be simultaneous with the disposing of the paper towel 40, or it may be delayed to provide sufficient time for the user to first use the towel 40 dispensed from the towel dispensing means 20. The user may discard the paper towel 40, e.g., to the bottom of the washing and drying chamber 12, at any time during the drying cycle. In this manner, the user obtains the combined drying advantages of a towel 40 and directed air drying (e.g., heated air drying), resulting in clean, dry hands in a matter of seconds. Moreover, since the drying cycle requires only a few seconds of drying (heated) air, the user's hands are not burned or otherwise irritated after extended and/or repeated use. The user then withdraws his or her hands from the washing and drying chamber 12.

The withdrawal of the user's hands is detected by the sensors 54, which then provide a detection signal to the control unit 56 to activate a waste disposal cycle. Alternatively, the waste disposal means 22 may be activated simultaneously with the blow drying means 20. In either case, in the preferred embodiment the blender 43 is activated creating a fluid vortex in the blender cup 45, and the blender 43 is operated for a time sufficient to disintegrate any waste matter, including spent towels 40, collected in the bottom of the washing and drying chamber, to liquify the used wash water and disintegrated waste matter, and to exhaust/ discharge the disintegrated waste matter and waste water from the washing and drying chamber through the exhaust port 46 formed in the side wall of the blender cup 45. In this manner, the blender 43 processes and discharges the waste material and waste water, e.g., via the drain 35 to a common sewage line, sink line or storage tank.

FIG. 2 also illustrates an optional exterior manual control means. In this embodiment, three foot pedals W,R,D are provided for operating a Washing cycle, a Rinsing cycle, and a Drying/Disposing cycle, respectively. The foot pedals are electronically connected to the control unit 56 of the control means 24, and may be used to selectively control the respective cycles, either independently of, or in conjunction with, an automatic cycle sequence programmed in the control unit 56. Those skilled in the art readily will be able to select alternative external control devices, such as audio/microphone driven control devices, and control sequences for achieving the desired function.

FIG. 1 also illustrates an optional audio/visual display 58. The audio/visual display may be a simple chart with written instructions for the user.

Alternatively, the display 58 may be an audio speaker, an LED display, an electronic video monitor, or any combination thereof, and the control unit 56 of the control means 24 may be electronically connected to the display 58 to provide instructions to the user. Those skilled in the art readily will recognize numerous alternative embodiments for providing such instructions.

Figure 5:
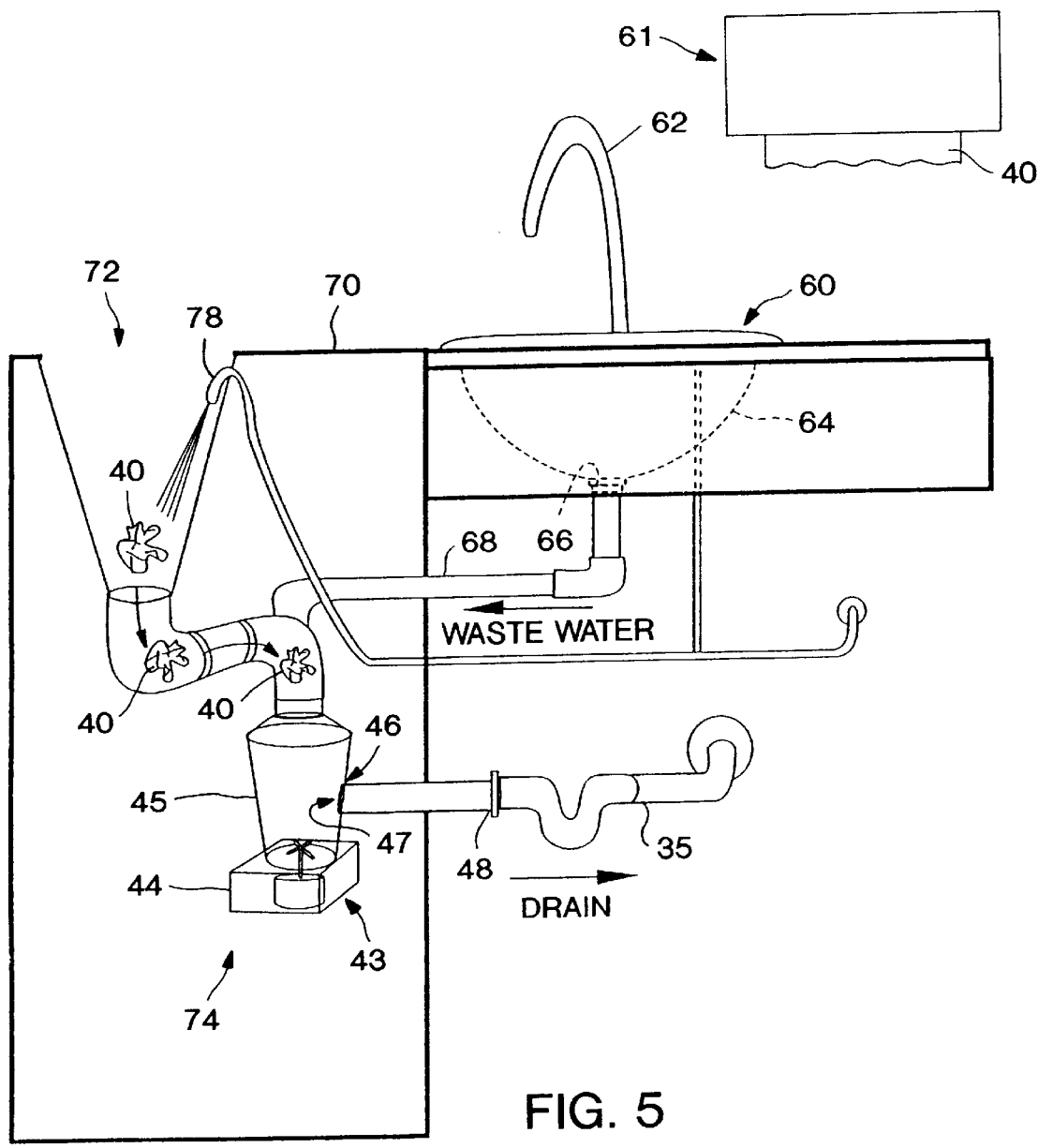
FIG. 5 schematically illustrates another hand washing and drying system utilizing a disposal apparatus and method of the present invention.

FIG. 5 schematically illustrates another aspect of the present invention, wherein a disposal apparatus is provided for use with an existing wash station. In this embodiment, the existing wash station includes a conventional sink 60, e.g., for use with a conventional towel dispenser 61. The sink 60 includes a faucet 62, a basin 64, a drain 66 and an exhaust line 68. The disposal apparatus includes a housing 70 forming a collection port 72 and housing a disposal unit 74. The collection port 72 may be generally funnel shaped, or tapered, to facilitate collection of spent towels, as is known in the art. The disposal unit 74 is arranged in fluid communication with the collection port 72 for recieving spent towels. The disposal apparatus preferably is provided with a liquid source 78, such as a liquid spray spout, for facilitating transport of spent towels from the collection port 72 to the disposal unit 74 and/or for liquifying disintegrated towels. The exhaust line 68 of the wash station 60 also is preferably provided in fluid communication with the collection port 72 or the disposal unit 74, thereby providing an additional or alternative liquid source to facilitate transport of spent towels from the collection port 72 to the disposal unit 74 and/or to liquify disintegrated towels.

Figure 6:
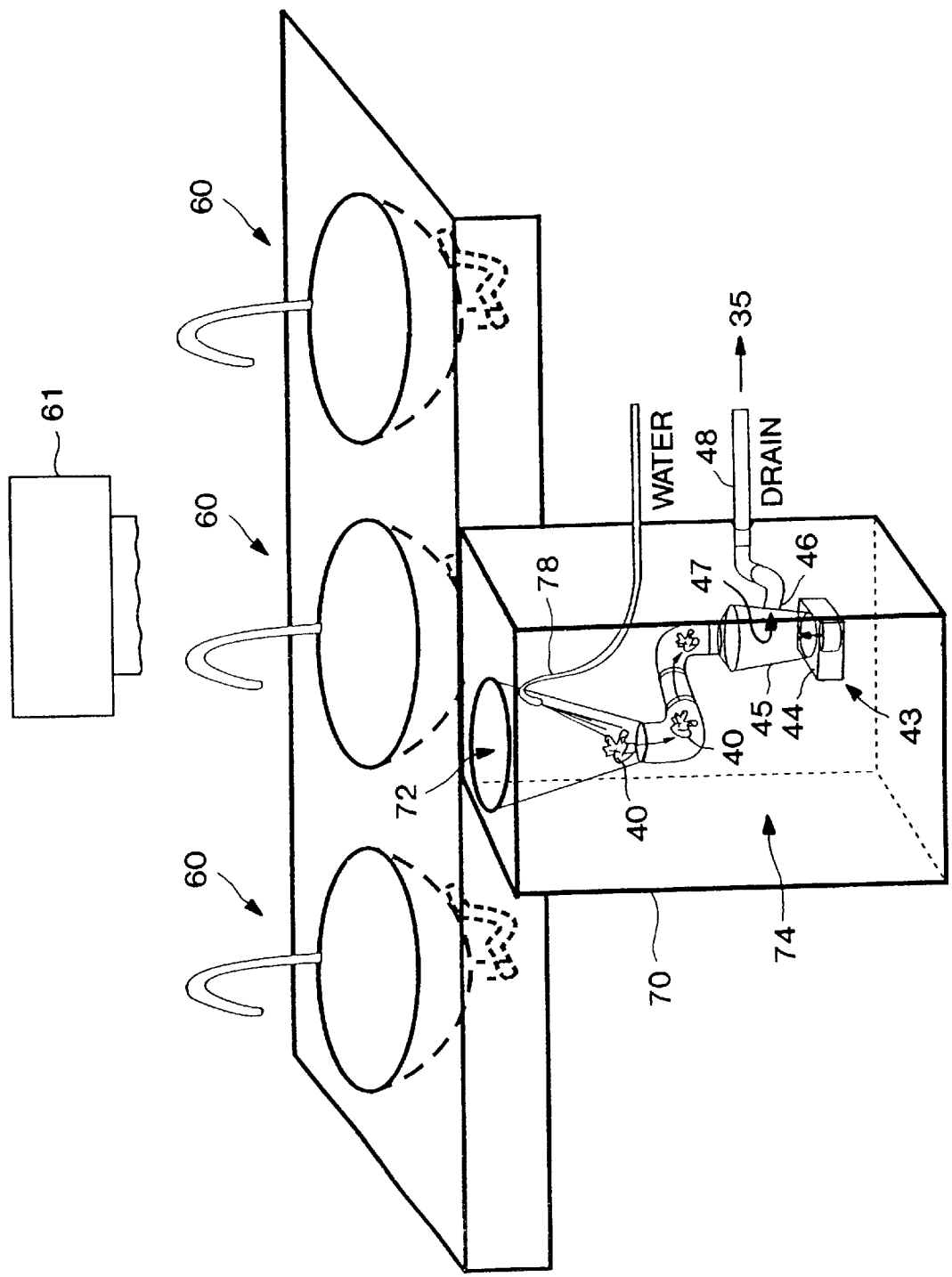
FIG. 6 schematically illustrates a further hand washing and drying system utilizing a disposal apparatus and method of the present invention.

FIG. 6 schematically illustrates a further aspect of the present invention, wherein a disposal apparatus is provided for use with an existing wash station. In this embodiment, the existing wash station similarly includes at least one conventional sink 60 for use with a conventional towel dispenser 61. However, in this embodiment, the disposal apparatus is provided with discrete plumbing that is not in fluid communication with any of the conventional sinks 60.

The disposal apparatus similarly includes a housing 70 forming a collection port 72 and housing a disposal unit 74. The disposal unit 74 is arranged in fluid communication with the collection port 72 for recieving spent towels, and is provided with a liquid source 78, such as a liquid spray spout, for facilitating transport of spent towels from the collection port 72 to the disposal unit 74 and for liquifying disintegrated towels.

As in the embodiment of FIG. 1, the disposal unit in each of the FIGS. 5 and 6 preferably is a blender 43, such as a conventional Osterizer® Imperial Cycle kitchen blender, including a base (with a motor and rotor/blade) 44 and a blender cup 45. The open end (top) of the blender cup 45 is provided in fluid communication with the collection port 72, thereby forming a collection port 42 through which spent paper towels and liquid may be collected. An opening 47 is formed in the side wall of the blender cup 45 and a waste fluid exhaust line 48 is provided in fluid communication with the interior of the blender cup through this opening 47, thereby forming an exhaust port 46 through which liquid and disintegrated paper towel waste matter may be exhausted/discharged from the blender cup 45 to the drain 35.

In each of these two embodiments (FIGS. 5 and 6), when operated, spent towels deposited in the collection port 72 are transported to the disposal unit 74/blender 43 by liquid from liquid source 78, either alone or in combination with liquid from waste water exhaust line 68. A spent towel and liquid then are collected in the blender cup 45 and liquified by disintegrating the spent towel and blending it with the liquid and/or used wash water in the blender cup 45 sufficient to allow the waste water and disintegrated waste matter to flow without clogging through the waste fluid exhaust line 48. It will be appreciated that this blending operation causes the waste water and disintegrated waste matter to form a fluid vortex in the blender cup 45. In this manner, the blender 43 acts as a centrifugal pump to exhaust/discharge the waste water and disintegrated waste matter out through the exhaust port 46 and exhaust line 48 to the drain 35.

Accordingly, it will be appreciated that the above disclosed embodiments achieve all of the objectives, advantages and features recited above.

Although specific embodiments of the present invention have been described above in detail, it will be understood that this description is merely for purposes of illustration. Various modifications of and equivalent structures corresponding to the preferred embodiments in addition to those described above may be made by those skilled in the art without departing from the spirit of the present invention which is defined in the following claims, the scope of which is to be accorded the broadest interpretation so as to encompass such modifications and equivalent structures.

What is claimed is:

1. A disposal apparatus for use with a wash station and a towel dispenser, the disposal apparatus comprising:
   a liquid source; and
   a waste disposal unit having a base portion and a chamber portion above the base portion, where said waste disposal unit is arranged in fluid communication with the liquid source and (i) collects liquid from said liquid source and receives a spent towel dispensed from said towel dispenser, (ii) disintegrates the spent towel and generates a fluid vortex of liquid and disintegrated spent towel in the chamber portion above the base portion, and (iii) exhausts the fluid vortex from an upper portion of the chamber portion.

2. The disposal apparatus of claim 1, wherein the waste disposal unit comprises a blender.

3. The disposal apparatus of claim 2, wherein said blender exhausts the fluid vortex by centrifugal effect.

4. The disposal apparatus of claim 3, wherein said blender comprises a base, a cup and a rotor that disintegrates the spent towel and generates the fluid vortex of disintegrated towel and liquid in said cup.

5. The disposal apparatus of claim 4, wherein said blender exhausts the fluid vortex through an opening in a side of the cup.

6. The disposal apparatus of claim 1, wherein the waste disposal unit exhausts the fluid vortex by centrifugal effect.

7. The disposal apparatus of claim 6, wherein the fluid vortex has an upper portion and a lower portion, and the waste disposal unit exhausts the fluid vortex at the upper portion.

8. The disposal apparatus of claim 1, wherein the wash station is integral with the disposal apparatus, and is provided in fluid communication with the disposal apparatus.

9. The disposal apparatus of claim 8, wherein the wash station comprises a washing and drying chamber, and the towel dispenser is arranged in communication with the interior of the washing and drying chamber.

10. The disposal apparatus of claim 1, wherein said waste disposal unit exhausts the fluid vortex into a standard plumbing line.

11. A disposal apparatus for use with a wash station and a towel dispenser, the disposal apparatus comprising:

a liquid source; and a waste disposal unit arranged in fluid communication with the liquid source that (i) collects liquid from said liquid source and receives a spent towel dispensed from said towel dispenser, (ii) disintegrates the spent towel and generates a fluid vortex of liquid and disintegrated spent towel, and (iii) exhausts the fluid vortex, wherein the wash station is integral with the disposal apparatus, and is provided in fluid communication with the disposal apparatus, and wherein the wash station comprises a washing and drying chamber, and the towel dispenser is arranged in communication with the interior of the washing and drying chamber.

* * * * *